United States Patent
Cressman

(10) Patent No.: US 9,848,934 B2
(45) Date of Patent: *Dec. 26, 2017

(54) THERMOCHEMICAL ABLATION OF BODILY TISSUE

(71) Applicant: Regents of the University of Minnesota, Minneapolis, MN (US)

(72) Inventor: Erik N.K. Cressman, Lake Elmo, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 418 days.

This patent is subject to a terminal disclaimer.

(21) Appl. No.: 14/589,211

(22) Filed: Jan. 5, 2015

(65) Prior Publication Data
US 2015/0173821 A1    Jun. 25, 2015

Related U.S. Application Data

(63) Continuation of application No. 14/081,001, filed on Nov. 15, 2013, now Pat. No. 8,926,586, which is a continuation of application No. 13/716,410, filed on Dec. 17, 2012, now Pat. No. 8,585,691, which is a continuation of application No. 12/528,015, filed as application No. PCT/US2008/054556 on Feb. 21, 2008, now Pat. No. 8,343,095.

(60) Provisional application No. 60/891,793, filed on Feb. 27, 2007.

(51) Int. Cl.
A61B 18/06      (2006.01)
A61B 18/00      (2006.01)

(52) U.S. Cl.
CPC .... *A61B 18/06* (2013.01); *A61B 2018/00577* (2013.01); *A61B 2018/068* (2013.01)

(58) Field of Classification Search
CPC ... A61B 18/06; A61B 2018/066; A61B 19/54; A61B 2090/3904; A61B 90/39; A61B 2505/05; A61B 2018/068; A61B 2018/00577; A61M 5/007; A61M 5/162; A61M 39/0247; A61M 25/007
See application file for complete search history.

(56) References Cited

U.S. PATENT DOCUMENTS

| | | | |
|---|---|---|---|
| 5,045,056 A | 9/1991 | Behl | |
| 5,797,869 A | 8/1998 | Martin et al. | |
| 6,165,201 A * | 12/2000 | Sawhney | A61B 17/00491 604/197 |
| 6,626,902 B1 | 9/2003 | Kucharczyk et al. | |
| 6,824,555 B1 | 11/2004 | Towler et al. | |

(Continued)

FOREIGN PATENT DOCUMENTS

| | | |
|---|---|---|
| JP | 2002-502278 | 1/2002 |
| JP | 2005-506101 | 3/2005 |

(Continued)

OTHER PUBLICATIONS

Araki et al., "Hepatocellular carcinoma treated by percutaneous hot saline injection," *Oncology Reports*, 12: 569-571, 2004.

(Continued)

*Primary Examiner* — Theodore Stigell
(74) *Attorney, Agent, or Firm* — Fish & Richardson P.C.

(57) ABSTRACT

Thermochemical ablation techniques may provide ablation of bodily tissue using chemical reaction energy.

10 Claims, 3 Drawing Sheets

(56) References Cited

U.S. PATENT DOCUMENTS

| | | | |
|---|---|---|---|
| 6,958,059 B2 | 10/2005 | Zadno-Azizi | |
| 8,343,095 B2* | 1/2013 | Cressman | A61B 18/06 604/82 |
| 8,585,691 B2* | 11/2013 | Cressman | A61B 18/06 604/257 |
| 8,926,586 B2* | 1/2015 | Cressman | A61B 18/06 604/506 |
| 8,979,831 B2* | 3/2015 | Cressman | A61B 18/06 604/113 |
| 2002/0120238 A1 | 8/2002 | McGuckin, Jr. et al. | |
| 2002/0143302 A1 | 10/2002 | Hinchleffe et al. | |
| 2003/0187411 A1 | 10/2003 | Constantz | |
| 2003/0226566 A1 | 12/2003 | Dhuper et al. | |
| 2004/0166062 A1 | 8/2004 | Roberts et al. | |
| 2005/0187542 A1 | 8/2005 | Auge, II et al. | |
| 2006/0079869 A1 | 4/2006 | Bischof et al. | |
| 2007/0191781 A1 | 8/2007 | Richards et al. | |
| 2008/0171982 A1 | 7/2008 | Mehier | |
| 2011/0152852 A1 | 6/2011 | Cressman | |
| 2012/0253192 A1 | 10/2012 | Cressman | |
| 2013/0131659 A1 | 5/2013 | Cressman | |
| 2014/0074063 A1 | 3/2014 | Cressman | |

FOREIGN PATENT DOCUMENTS

| | | |
|---|---|---|
| WO | WO 98/52480 | 11/1998 |
| WO | WO 00/09199 | 2/2000 |
| WO | WO 02/067796 | 9/2002 |
| WO | WO 03/080151 | 10/2003 |
| WO | WO 2008/106357 | 9/2008 |
| WO | WO 2008/108357 | 9/2008 |
| WO | WO 2010/014658 | 2/2010 |

OTHER PUBLICATIONS

Arrivé et al., "Percutaneous acetic acid injection for hepatocellular carcinoma: using CT fluoroscopy to evaluate distribution of acetic acid mixed with an iodinated contrast agent," *AJR Am J Roentgenol.*, 180(1):159-162, 2003.

Castaneda and Kinne, "Cytotoxicity of millimolar concentrations of ethanol on HepG2 human tumor cell line compared to normal rat hepatocytes in vitro," *J. Cancer Res. Clin. Oncol.*, 126(9):503-510, Sep. 2000.

Castaneda and Kinne, "Short exposure to millimolar concentrations of ethanol induces apoptotic cell death in multicellular HepG2 spheroids," *J. Cancer. Res. Clin. Oncol.*, 126(6):305-310, Jun. 2000.

Clark et al., "Chemical Ablation of Hepatocellular Carcinoma," *JVIR*, vol. 13, No. 9, Part 2, Sep. 2002, pp. S246-S252.

Clark, "Chemical Ablation of Liver Cancer," *Techniques in Vascular and Interventional Radiology*, 10(1):58-63, Mar. 2007.

Cressman, E.N.K., "A New Hydrophobic Gel Phantom Gel for Study of Thermochemical Ablation: Initial Results Using a Weak Acid and Weak Base," Abstract 434, p. S154, *2007 SIR $32^{nd}$ Annual Scientific meeting*, Mar. 1-6, 2007, Seattle, WA.

Finch, et al., "The use of a 'Liquid' Electrode in Hepatic Electrolysis," *Journal of Surgical Research*, 120, 272-277 (2004).

Frank et al., Exothermic Electrophiles for Thermochemical Ablation Assessed in a Gel Phantom,: *SIR 2008 33rd Annual Scientific Meeting*, Abstract No. 278, 1 page, 2008.

Glinos, et al., "Cytokinetic and Cytotoxic Effects of Urea on HeLa Cells in Suspension Cultures," J. Nat'l Cancer Inst., 71: 1211-1219, Dec. 1983.

Goldberg et al., "Radio-Frequency Thermal Ablation with NaCl Solution Injection: Effect of Electrical Conductivity Tissue Heating Coagulation—Phantom and Porcine Liver Study," *Radiology*, 2001; 219:157-165.

Hiltbrand et al. "A new method of thermoablation with hot water vapour for localized tumours," *Anticancer Research*, 24(5A):2757-2763, Sep.-Oct. 2004.

Kim et al., "Combined radiofrequency ablation and hot saline injection in rabbit liver," *Invest Radiol.*, 38(11):725-732, 2003.

Kurokohchi et al. "Percutaneous ethanol and lipiodol injection therapy for hepatocellular carcinoma," *International Journal of Oncology*, 24: 381-387, 2004.

Liao et al., "Radiofrequency ablation after transarterial embolization as therapy for patients with unresectable hepatocellular carcinoma," *Eur J Surg Oncol.* 34(1): 61-66, 2008.

Lubienski et al. "Radiofrequency Themial Ablation: Increase in Lesion Diameter with Continuous Acetic Acid Infusion" *Cadiovasc Intervent Radiol.*, 28:789-794, 2005.

Nanz, et al., "Contrast Material—enhanced Visualization of the Ablation Medium for Magnetic Resonance—monitored Ethanol Injection Therapy: Imaging and Safety Aspects," *J. Vascular and Interventional Radiology*, vol. 17(1) Jan. 2006. 95-102.

Parmley, et al., "The Possible Deleterious Effects of the Intramyometrial Injection of Hypertonic Urea," *Obstetrics & Gynecology*, Jun. 16, 1975, 3 pages.

Puls, et al., "Laser-Induced Thermotherapy (LITT) of Liver Metastases: MR-Guided Percutaneous Insertion of an MRI-Compatible Irrigated Microcatheter System Using a Closed High-Field Unit," *Journal of Magnetic Resonance Imaging*, 17:663-670, (2003).

Weinberg et al., "Combined radiofrequency ablation and doxorubicin-eluting polymer implants for liver cancer treatment," Published online Nov. 21, 2006 in Wiley InterScience (www.interscience.wiley.com), DOI: 10.1002/jbm.a.30926, 9 pages.

Wilson, Elizabeth, "A Renaissance for Hofmeister," *Chemical & Engineering News: Science & Technology*, Nov. 26, 2007, vol. 85, No. 48, pp. 47-49.

Australian Patent Examination Report No. 1 for Application No. 2008219461, dated Oct. 26, 2012, 3 pages.

European Search Report for Application No. 08730371.5, dated Oct. 22, 2012, 6 pages.

International Preliminary Report on Patentability, PCT/US2008/054556, dated Sep. 11, 2009, 6 pages.

International Search Report and Written Opinion, PCT/US2008/054556, dated Jul. 28, 2008, 12 pages.

Japanese Office Action in Application No. 2009-551790, dated Aug. 15, 2012, 4 pages.

Office Action; dated May 13, 2013; Japan; 2009-551790; 4 pages.

Office Action; dated Sep 10, 2013; Australia; 2008219461; 3 pages.

* cited by examiner

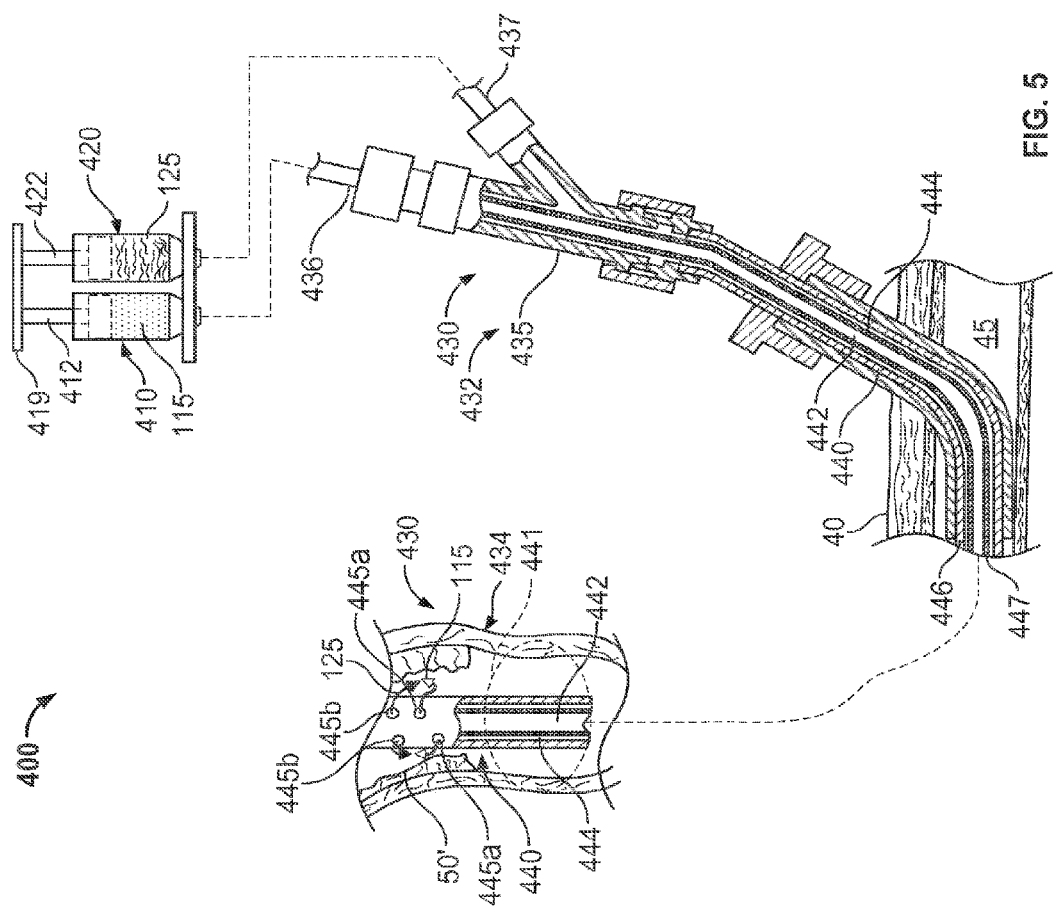

THERMOCHEMICAL ABLATION OF BODILY TISSUE

CROSS-REFERENCE TO RELATED APPLICATION(S)

This application is a continuation of U.S. patent application Ser. No. 14/081,001 filed on Nov. 15, 2013, (U.S. Pat. No. 8,926,586) and entitled "Thermochemical Ablation of Bodily Tissue," which is a continuation of U.S. patent application Ser. No. 13/716,410 filed on Dec. 17, 2012 (U.S. Pat. No. 8,585,691) and entitled "Thermochemical Ablation of Bodily Tissue," which is a continuation of U.S. patent application Ser. No. 12/528,015 filed on Jan. 26, 2010 (U.S. Pat. No. 8,343,095) and entitled "Thermochemical Ablation of Bodily Tissue," which is a National Stage application under 35 U.S.C. §371 and claims benefit under 35 U.S.C. §119(a) of International Application No. PCT/US2008/054556, filed Feb. 21, 2008, and entitled "Thermochemical Ablation of Bodily Tissue", which claims priority to U.S. Application No. 60/891,793 filed on Feb. 27, 2007 and entitled "Thermochemical Ablation of Bodily Tissue." The entire disclosures of these earlier applications are incorporated herein by reference.

TECHNICAL FIELD

This document relates to delivery of chemical reagents to targeted bodily tissue, for example, to provide thermochemical ablation therapy.

BACKGROUND

A number of ablation treatments have been used to treat tumors or other tissue in a patient's body. In some cases, ablation therapy may be used to treat tumors that are not responsive to chemotherapy or other techniques. For example, primary liver cancer or hepatocellular carcinoma (HCC) is an aggressive neoplasm that may not respond well to intravenous chemotherapy.

The choice of treatment for HCC normally depends on severity of underlying liver disease, size and number of lesions, location of lesions, ability to detect them with MRI, non-contrast or contrast CT, or ultrasound, and local expertise. Conventionally, physicians have employed RF ablation or microwave ablation to destroy the tumor tissue with heat, combined heating with coadministration of liposomes containing a drug, cryoablation to freeze a tumor, hepatic arterial drug infusion, bland arterial embolization, chemotherapy combined with arterial embolization, selective internal radioembolization using radioactive labeled iodized oil or radioactive microspheres as the embolic agent, external beam radiation therapy, or direct injection of a single agent (e.g., ethanol, acetic acid, hydrochloric acid, hot saline, or sodium hydroxide) to ablate the tumor.

One low cost and less invasive method is percutaneous injection of one of either ethanol or acetic acid. Although high-cost RF or microwave ablation systems are generally not employed with this method, conventional single-agent injections have raised concerns. The injection of a single agent such as acetic acid may increase the acid load in the patient, which cause toxicity problems and possibly renal failure. The injection of a single agent such as ethanol can also cause toxicity problems. To regulate the acid load or other toxicity problems from the injections of the single chemical agent, the dosage for each session is usually limited. Smaller dosages of the agent may generally limit the physician's ability to treat anything other than smaller tumors.

SUMMARY

Some thermochemical ablation techniques may provide minimally invasive ablation of solid tumors such as liver cancer, lung cancer, renal cancer, breast cancer, prostate cancer, sarcomas, metastatic disease, or the like. These ablation techniques may induce chemical reactions to generate heat for ablation energy (e.g., employing chemical reaction energy rather than electrical energy, magnetic energy, or direct chemical toxic effects). Such chemical reactions may be induced by mixing at least one acid reagent and at least one base reagent, which can neutralize the acid load applied to the patient during the procedure. In some circumstances, the concentration of the base reagent or the acid reagent can be selected so as to partially neutralize the acid or base load while generating heat energy, thereby providing heated solution with a limited and safe level of remaining acid or base load. Accordingly, the techniques described herein may permit a physician to simultaneously infuse at least two thermochemical ablation reagents without mixing the reagents until the reagents reach the distal portion of the delivery cannula.

In some embodiments, a thermochemical ablation system may include a percutaneous fluid delivery cannula comprising first and second lumens extending from a proximal portion to a distal portion. The distal portion may have a first side port in fluid communication with at least the first lumen and a second side port in fluid communication with at least the second lumen. The system may also include a first reservoir that contains a first thermochemical ablation reagent so as to communicate the first thermochemical ablation reagent through the first lumen to the distal portion of the percutaneous fluid delivery cannula. The portion of the first thermochemical ablation reagent can be deliverable out of the first side port. The system may further include a second reservoir that contains a second thermochemical ablation reagent so as to communicate the second thermochemical ablation reagent through the second lumen to the distal portion of the percutaneous fluid delivery cannula. The portion of the second thermochemical ablation reagent can be deliverable out of the second side port to provide simultaneous radial dispersion and mixing of the first and second thermochemical ablation reagents at the distal portion.

Particular embodiments of a device to ablate bodily tissue may include a multi-lumen thermochemical ablation cannula to simultaneously infuse at least two thermochemical ablation reagents into targeted tissue proximate a distal portion of the cannula. The distal portion of the cannula may include a plurality of fluid ports to dispense at least two thermochemical ablation reagents and thereby mix the at least two thermochemical ablation reagents proximate a distal portion of the cannula. When the at least two thermochemical ablation reagents are dispensed from the plurality of fluid ports, the thermochemical ablation reagents can mix with one another to generate an exothermic chemical reaction sufficient to ablate tissue.

In some embodiments, a method for thermochemical ablation of targeted tissue may include delivering a first thermochemical ablation reagent through a first lumen of a percutaneous injection needle. The method may also include delivering a second thermochemical ablation reagent through a second lumen of the percutaneous injection needle. The method may further include simultaneously infusing first and second thermochemical ablation reagents into targeted tissue to radially disperse and mix the first and second thermochemical ablation reagents at a distal portion of the injection needle.

Some or all of these embodiments may provide one or more of the following advantages. First, the thermochemical ablation techniques may provide minimally invasive ablation of solid tumors (e.g., liver cancer, lung cancer, renal cancer, breast cancer, prostate cancer, sarcomas, or the like) or other tissues including varicoceles, varicose veins, or the like. Such techniques may be useful, for example, to treat patients who are not surgical candidates due to the nature of the tumors or other intervening factors. Second, the thermochemical ablation techniques may induce chemical reactions to generate heat either to be the primary ablation source or to augment another ablation source (e.g., RF ablation, microwave ablation, denaturant sources such as sclerosants, detergents, or urea, or other ablation sources). Third, the chemical reactions may be induced by mixing at least one acid reagent and at least one base reagent, thereby reducing or eliminating the acid or base load applied to the tissue. Because the acid or base load is reduced or eliminated, a larger dose of reagents may be applied without causing toxicity problems. Furthermore, in some embodiments, the salt byproducts from the mixing of the first and second thermochemical ablation reagents can be highly hyperosmolar, thereby creating a local environment incompatible with cell survival in the treated tissue after the heat energy is applied. Fourth, some of the systems and devices described herein may be manufactured without high-cost components such as RF ablation probes. Fifth, the thermochemical ablation techniques described herein may be used to treat larger tumors in a lower number of treatment sessions, thereby adding convenience to the patient. Sixth, the thermochemical ablation process can be monitored in real-time using medical imaging systems, such as ultrasound imaging devices. Moreover, in some embodiments, the thermochemical ablation process can be monitored in an MRI setting without the need for specialize (high-cost), MRI-compatible alloys in the delivery device. Seventh, the devices described herein permit a physician to simultaneously infuse at least two thermochemical ablation reagents without mixing the reagents until the reagents reach the distal portion of the delivery cannula. As such, some embodiments of the delivery device can be used to provide the ablation heat energy to internal body tissue without the requirement for outer layers of thermal insulation that may otherwise increase the outer size of the delivery device (and the delivery pathway through the tissue). Eighth, the delivery cannula may include a number of side ports that provide radial dispersion of the reagents when exiting the cannula, thereby promoting mixing (e.g., more turbulence) and distributing the ablation heat energy in a more even manner. Moreover, the first and second thermochemical ablation reagents can provide an ablative effect that causes more even shaping in the treated area (as compared to a direct injection of acetic acid or ethanol) due to the conductive effects of heat into the surrounding tissue. Ninth, in some circumstances, a portion of the first and second reagents can mix with one another within the distal portion of the cannula before dispensation into the targeted tissue. By mixing at least a portion of the first and second thermochemical ablation reagents in the distal portion, some portion of the dispensed fluid can be heated from the exothermic chemical reaction immediately before dispensation into the targeted tissue.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5 is a section view of an alternative embodiment of a thermochemical ablation system.

Like reference symbols in the various drawings indicate like elements.

DETAILED DESCRIPTION OF ILLUSTRATIVE EMBODIMENTS

A thermochemical ablation system may employ minimally invasive techniques to ablate solid tumors or other targeted tissue. These ablation techniques may induce chemical reactions to generate heat for ablation energy. Such chemical reactions may be induced by mixing at least one acid reagent and at least one base reagent, which can neutralize or otherwise reduce the acid or base load applied to the patient during the procedure. Because the acid or base load is reduced or eliminated, a larger dose of reagents may be applied and a greater level of ablation energy may be achieved without causing toxicity buildup in the patient. In some embodiments, a thermochemical ablation system enables a physician to simultaneously infuse at least two thermochemical ablation reagents without mixing the reagents until the reagents reach the targeted tissue.

The thermochemical ablation techniques described herein can be used to treat solid tumors that arise in number of circumstances, including liver cancer, lung cancer, renal cancer, breast cancer, prostate cancer, sarcomas, or the like. These techniques may be useful, for example, to treat patients who are not surgical candidates due to the nature of the tumors or other intervening factors. For example, some patients with HCC or other types of liver cancer are not candidates for surgery. The thermochemical ablation system described herein may be effective in the treatment of such liver cancer in a manner that is relatively convenient to the patient (e.g., possibly reducing the number of treatment sessions) and relatively cost-effective for the medical care provider (e.g., not necessarily requiring high-cost equipment such as RF ablation probes or the like).

Figure 1:
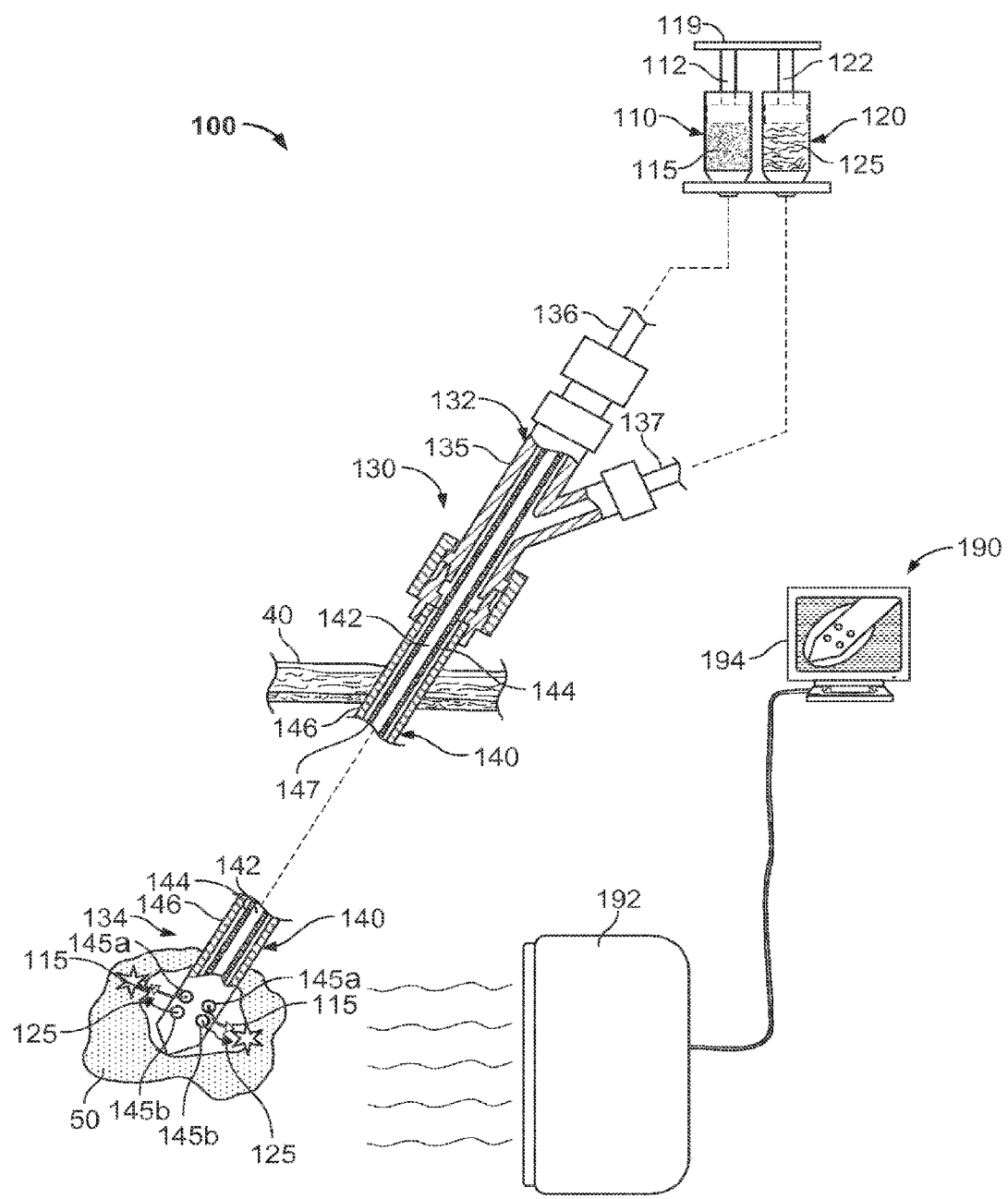
FIG. 1 is a section view of a thermochemical ablation system, in accordance with some embodiments.

Referring to FIG. 1, a thermochemical ablation system 100 is capable of infusing thermochemical ablation reagents into targeted tissue 50 to induce a chemical reaction and thereby ablate the tissue 50. The system 100 includes a first fluid reservoir 110 and a second fluid reservoir 120 that are in fluid communication with a thermochemical ablation device 130. The first reservoir 110 may include a first thermochemical ablation reagent 115 (such as an acid reagent), and the second reservoir 120 may include a second thermochemical ablation reagent 125 (such as a base reagent). Also, each of the reservoirs 110 and 120 includes an actuator 112 and 122 that can be adjusted to provide a dispensing force to the reagents 115 and 125. Accordingly, the first and second reservoirs 110 and 120 can be actuated to deliver both reagents 115 and 125 to a proximal portion 132 of the fluid delivery device 130, which then passes the reagents 115 and 125 to a distal portion 134 of the device 130. In this embodiment, the first actuator 112 and the second actuator 122 are coupled to one another with a coupling 119 so that both actuators 112 and 122 can be simultaneous adjusted. For example, a user may apply a force to the coupling 119 to contemporaneously adjust the actuators 112 and 122, which causes the first and second reagents 115 and 125 to be simultaneously delivered to the device 130. In another example, a physician or other user may selectively activate a computer-controlled mechanism that acts upon the coupling 119 to provide the adjustment force. Such a computer-controlled mechanism may provide for accurate dosages of the reagents 115 and 125 delivered from the reservoirs 110 and 120. In other embodiments, the first and second reservoirs 110 and 120 may not be coupled to one another, and the actuators 112 and 122 may be separately adjusted to dispense the reagents simultaneously or in selected sequence.

In this embodiment, the thermochemical ablation device 130 includes a multi-lumen cannula 140 that can simultaneously infuse the first and second thermochemical ablation reagents 115 and 125 into the targeted tissue 50 proximate the distal portion 134. In particular, the cannula 140 includes a first lumen 142 in fluid communication with the first reservoir 110 to deliver the first thermochemical ablation reagent 115 to the distal portion 134. Also, the cannula 140 includes a second lumen 144 in fluid communication with the second reservoir 120 to deliver the second thermochemical ablation reagent 125 to the distal portion 134. The distal portion 134 of the cannula 140 may include a plurality of fluid ports 145a-b to radially disperse the first and second thermochemical ablation reagents 115 and 125 and thereby mix the reagents 115 and 125 in the region proximate the distal portion 134. It should be understood that, in other embodiments, three or more reservoirs may be used to deliver three or more thermochemical ablation reagents to the targeted tissue 50. In such circumstances, thermochemical ablation device may include a multi-lumen cannula having three or more lumens, each of which being in fluid communication with an associated fluid reservoir.

Still referring to FIG. 1, this embodiment of the fluid delivery device 130 includes a cannula 140 in the form of a percutaneous injection needle. For example, the cannula 140 may includes a generally rigid needle body 146 having an outer diameter of about 0.135 inches or less, about 0.120 inches to about 0.008 inches, and about 0.072 inches to about 0.028 inches. The needle body 146 may comprise stainless steel or another generally rigid material that is suitable for percutaneous insertion through the patient's skin 40. Furthermore, the distal tip portion of the cannula 140 may include a pointed tip so as to facilitate penetration through the skin 40 and toward the targeted tissue 50. The cannula 140 may also include an internal tube 147 that passes through the needle body 146. In this embodiment, the internal tube 147 comprises a second, smaller needle body that is generally coaxial with the outer needle body 146, thereby defining the first lumen 142 within the second lumen 144. It should be understood that, in other embodiments, the first and second lumens 142 and 144 may be configured to have a side-by-side arrangement (refer, for example, to FIG. 3). In such circumstances, the first and second lumens 142 and 144 may be defined by two bores that are formed through the outer needle body 146 (e.g., without using a centrally located internal tube 147).

In some embodiments, the fluid delivery device 130 may be packaged as part of a thermochemical ablation kit, which the physician or other user can use without the need to further assemble any components of the device 130. For example, the fluid delivery device 130 may be manufactured so that outer needle body 146, the inner tube 147, and a valve device 135 are fully assembled and packaged into the kit. Also, the cannula 140 can be manufactured so that the first lumen 142 is in fluid communication with side ports 145a and the second lumen 144 is in fluid communication with the side ports 145b (described in more detail below, for example, in connection with FIGS. 2-4). In these circumstances, the physician or other user can readily unpackage the fluid delivery device 130 from the kit and thereafter connect both the first fluid line 136 of the fluid delivery device 130 to the first reservoir 110 and the second fluid line 137 to the second reservoir 120. Such fluid line connections permit the first and second reservoirs 110 and 120 to be in fluid communication with the first and second lumens 142 and 144.

As shown in FIG. 1, the distal portion 134 of the fluid delivery device 130 may include one or more side ports 145a-b through which the first and second reagents 115 and 125 are dispensed into the targeted tissue 50. The side ports 145a-b may be oriented so that the thermochemical ablation reagents 115 and 125 are radially dispersed from the distal portion 132. Such radial dispersion of the thermochemical ablation reagents may provide improved mixing of the reagents 115 and 125 upon exiting the fluid delivery device 130 (e.g., due to increased turbulence). Furthermore, the radial dispersion through the side ports 145a-b can more evenly distribute the heat generated by the mixing of the reagents 115 and 125.

The first set of side ports 145a may be in fluid communication with the first lumen 142 so that the first thermochemical ablation reagent 115 is evacuated from the side ports 145a when the coupler 119 (and first actuator 112) is adjusted. Likewise, the second set of side ports 145b may be in fluid communication with the second lumen 144 so that the second thermochemical ablation reagent 125 is evacuated from the side ports 145b when the coupler 119 (and second actuator 112) is adjusted. Accordingly, the fluid delivery device 130 provides for simultaneous infusion of the first and second reagents 115 and 125 into the targeted tissue 50, during which the thermochemical ablation reagents 115 and 125 mix with one another to cause an exothermic chemical reaction. If the first and second reagents 115 and 125 are to be infused in different proportions, the first reservoir 110 may have a different configurations (e.g., different cross-sectional areas) so that different amounts of fluid are dispensed when the actuators 112 and 122 are simultaneously adjusted (e.g., using the coupler 119). In some embodiments, the concentration of the base reagent or the acid reagent can be selected so as to fully neutralize the acid and base load applied to the targeted tissue 50 after the thermochemical ablation reaction. In other embodiments, the concentration of the base reagent or the acid reagent can be selected so as to partially neutralize the acid or base load while generating heat energy, thereby providing heated solution with a limited and safe level of remaining acid or base load.

The heat generated from this chemical reaction may be sufficient to ablate at least a portion of the targeted tissue 50 surrounding the distal portion 134 of the fluid delivery device 130. Because the fluid delivery device 130 infuses two reagents that chemically react with one another (rather than direct injection of a single acidic reagent), the byproducts of the chemical reaction may include greater heat generation with lower acid (or base) load toxicity. For example, in some embodiments, the fluid delivery device 130 can infuse both an acid reagent and a base reagent to create a larger lesion in the targeted tissue 50 (e.g., larger than would otherwise be obtained by direct injection acetic acid alone) while simultaneously reducing the acid load, whether by lesion expansion or by a thermal injury. Accordingly, the thermochemical ablation techniques described herein may be used to treat larger tumors in one or two sessions with fewer complications from acid (or base) load toxicity.

The thermochemical ablation reagents 115 and 125 that are infused into the targeted tissue 50 may be selected to provide a suitable energy deposition in tissue and to provide other features, such as hyperosmolarity. In some embodiments, the first thermochemical ablation reagent 115 may comprise an acid. For example, the first thermochemical ablation reagent 115 may comprise an acid selected from the group consisting of acetic acid, peracetic acid, hydrochloric acid, hydrobromic acid, hydriodic acid, sulfuric acid, nitric acid, nitrous acid, perchloric acid, phosphoric acid, oxalic acid, pyruvic acid, malonic acid, amino acids (e.g., carboxylic acid derivatives), and the like. Also in some embodiments, the second thermochemical ablation reagent 125 may comprise a base. For example, the second thermochemical ablation reagent 125 may comprise a base selected from the group consisting of KOH, NaOH, $NH_4OH$, $Ca(OH)_2$, $NaHCO_3$, $K_2CO_3$, BuLi, NaOEt or NaSEt (e.g., Na or K salts of alkoxides or thio analogues), NaH, KH, particular amines, and the like.

As previously described, the particular acid and the particular base may be selected to product the desired heat generation and low toxicity byproducts. For example, in some embodiments, the first thermochemical ablation reagent 115 may be either acetic acid or hydrochloric acid, and the second thermochemical ablation reagent 125 may be NaOH, NaOEt, or $NH_4OH$. Accordingly, the fluid delivery device 130 maintains the first thermochemical ablation reagent 115 separate from the second thermochemical ablation reagent 125 until the reagents 115 and 125 reach the distal portion 134 and are simultaneously infused into the targeted tissue 50 where the reagents 115 and 125 mix and chemically react with one another to generate the ablation heat energy. Moreover, the infusion of the base reagent in addition to the acid reagent can neutralize or other reduced the acid load applied to the patient during the treatment, thereby alleviating some of the problems associated with acid load toxicity. The byproducts from the chemical reaction of the first and second reagents 115 and 125 may further benefit the ablation process, for example, due to the hyperosmolarity of the environment.

It should be understood from the description herein that, in other embodiments, the thermochemical ablation reagents 115 and 125 may include other reactive substances. For example, the first thermochemical ablation reagent 115 may comprise electrophiles, and the second ablation reagent 125 may comprise nucleophiles. In some embodiments, the first thermochemical ablation reagent 115 may include an electrophile selected from the group consisting of acetic anhydride, acetyl chloride, acetyl bromide, other anhydrides, other acid halides, and the like. In these circumstances, the second thermochemical ablation reagent 125 may comprise a nucleophile selected from the group consisting of alkoxides, thio analogues, mercaptans (e.g., sulfhydryl), some amines, and the like. Other nucleophiles can include alcohols, sugar molecules, water, and endogenous nucleophiles. Furthermore, in some embodiments, the second thermochemical ablation reagent 125 may comprise a nucleophile selected from the group of previously described bases (e.g., NaOH, NaOEt, $NH_4OH$, or the like). Thus, some exemplary embodiments of the fluid delivery device 130 can infuse an electrophile (such as acetyl chloride) with a nucleophile (such as NaOH) that chemically react with one another. The byproducts of the chemical reaction may provide significant heat generation while at least partially neutralizing the acid (or base) load. Such thermochemical ablation techniques described herein may be used to treat larger tumors in relatively few sessions with reduced complications from acid or base load toxicity.

It should be understood from the description herein that, in other embodiments, the thermochemical ablation reagents 115 and 125 may include other reactive substances. For example, the first thermochemical ablation reagent 115 may comprise particular oxidizing agents, and the second ablation reagent 125 may comprise certain reducing agents. Finally, in some embodiments, the thermochemical ablation reagents could be chosen to have useful imaging or other analyzable features (e.g., fluorescence, nuclear isotopes, MR imaging characteristics, or the like) to permit a physician to evaluate the reagent distribution in the targeted tissue 50 and throughout the body.

In some embodiments, one or both of the thermochemical ablation reagents 115 and 125 may be mixed with a denaturing agent that enhances the tissue ablation process. For example, a denaturing agent such as a sclerosant, detergent, urea, or sodium perchlorite (or another substance from the Hofmeister series) can be added to the first reservoir 110 to mix with the first reagent 115 prior to injection through the delivery device 130. The denaturing agent may act upon the targeted tissue 50 to enhance the ablation effects caused by the thermochemical reaction of the first reagent 115 and the second reagent 125.

Moreover, in some embodiments, a drug may be added to one or both of the thermochemical ablation reagents 115 and 125 so as to provide a pharmacological effect on the targeted tissue in addition to the thermochemical ablation effects. In one example, a chemotherapy drug can be added to the second reservoir 120 to mix with the second reagent 125 prior to injection through the delivery device 130. The chemotherapy drug can be administered to the targeted tissue 50 through the delivery device 130 to provide pharmacological effects contemporaneously with the ablation effects from thermochemical reaction of the first reagent 115 and the second reagent 125.

Still referring to FIG. 1, some embodiments of the thermochemical ablation system 100 may include a medical imaging system that provides real-time monitoring of the device 130 insertion and the delivery of the reagents 115 and 125. For example, the medical imaging system can include an ultrasound imaging system 190 to enable a physician or other user to view the distal portion 134 of the fluid delivery device 130 in the targeted tissue 50. In this embodiment, the ultrasound imaging system 190 includes an ultrasound probe device 192 that can be manipulated on the outside of the patient's body or within a body cavity. The ultrasound probed 192 may be connected to an ultrasound display system 194 that interprets the signals from the probe 192 and generates a display of the targeted portion of the patient's body. For example, as shown in FIG. 1, the ultrasound display system 194 may show the distal portion 134 of the device 130 as it is inserted into the targeted tissue 50 for delivery of the thermochemical ablation reagents 115 and 125. It should be understood that, in other embodiments, the imaging system may comprise another type of system other than the ultrasound imaging system 190. For example, the medical imaging system may include a CT imaging system or the like. Some or all of the delivery device 130 may comprise materials that are compatible with the selected imaging system so as to enable monitoring of the delivery device 130 during insertion. For example, the cannula 140 may comprise a metallic material that can be visualized using the ultrasound imaging system 190. In another example, the distal portion 134 of the delivery device 130 may include magnetic resonance markers or other features that permit viewability using the selected imaging system. Furthermore, in some embodiments, the delivery device 130 may include depth markers that are directly viewable to the physician or other user. For example, the cannula 140 may include a number of depth markers on the outer surface of the needle body 146. The physician or other user can view these depth markers during insertion of the cannula 140 through the skin 40 to indicate the approximate depth of insertion.

Figure 2:
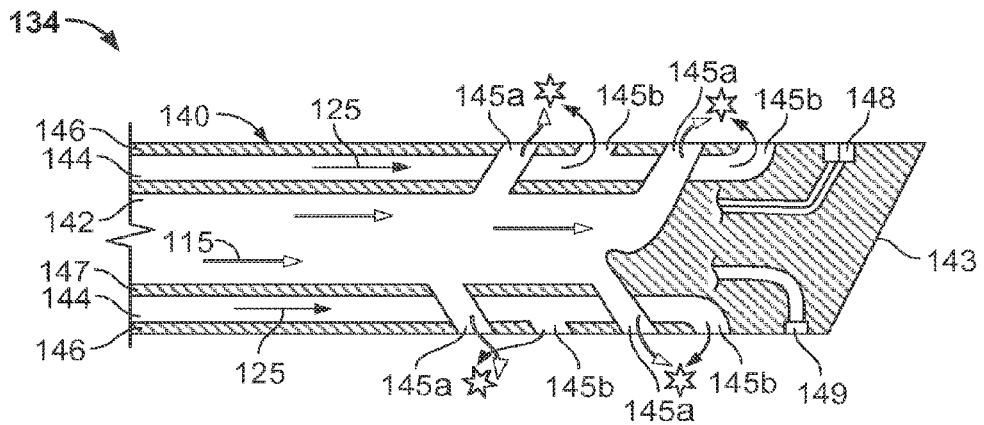
FIG. 2 is a cross-sectional view of a portion of a delivery cannula for a thermochemical ablation system, in accordance with some embodiments.

Referring to FIG. 2, the distal portion 134 of the fluid delivery device 130 may include one or more side ports 145a-b in the cannula 140. As previously described, the side ports 145a-b can be used to radially disperse the first and second thermochemical ablation reagents 115 and 125 and thereby mix the reagents 115 and 125 in the region proximate the distal portion 134. Such radial dispersion of the thermochemical ablation reagents can improve the mixing of the reagents 115 and 125 upon exiting cannula 140 (e.g., due to increased turbulence). The first and second lumens 142 and 144 maintain the reagents 115 and 125 separate from one another until they reach the distal portion 134 and are dispensed from the ports, after which the reagents are capable of generating an exothermic chemical reaction for ablating the targeted tissue. In such circumstances, the radial dispersion through the side ports 145a-b can more evenly distribute the heat generated by the mixing of the reagents 115 and 125.

Figure 3:
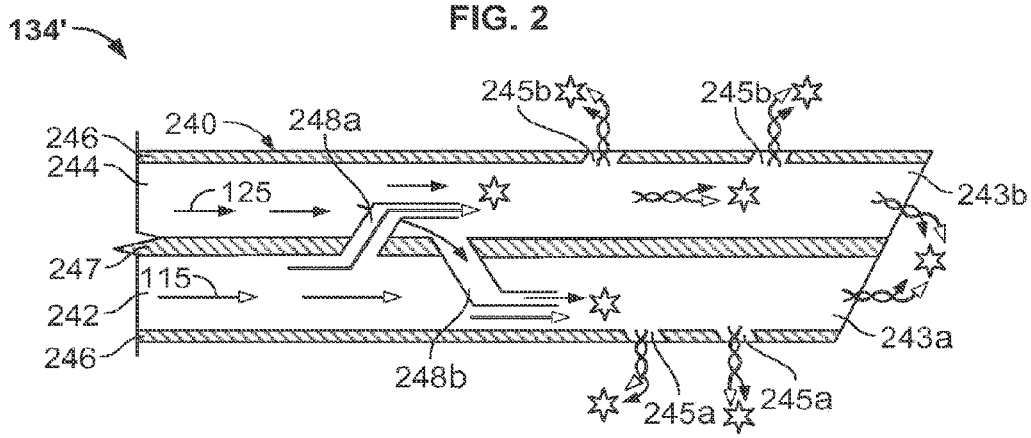
FIG. 3 is a cross-sectional view of a portion of an alternative delivery cannula for a thermochemical ablation system, in accordance with some embodiments.

It should be understood that, in some embodiments, the first and second thermochemical ablation reagents 115 and 125 may be at least partially mixed in the distal portion 134 immediately before being dispensed from the side ports 145a-b (refer, for example, to FIG. 3). Also, in other embodiments, the number of first side ports 145a and second side ports 145b may be different than that depicted in FIG. 2. For example, the cannula 140 may include only one first side port 145a and only one second side port 145b. In another example, the cannula 140 may include three, four, five, six, seven, eight, nine, ten, or more of the first side ports 145a. Also, the cannula 140 may include three, four, five, six, seven, eight, nine, ten, or more of the second side ports 145b. Furthermore, in some embodiments, the number of first side ports 145a may be different from the number of second side ports 145b. For example, the cannula 140 may include three of the first side ports 145a and four, five, or six of the second side ports 145b.

In this embodiment depicted in FIG. 2, the first lumen 142 is arranged coaxial with the second lumen 144. For example, the internal tube 147 may be disposed within the needle body 146 of the cannula 140 so as to define at least a portion of the first lumen 142 within the internal tube 147 and to define at least a portion of the second lumen 144 between the internal tube 147 and the needle body 146. The internal tube 147 may comprise a generally rigid material, such as stainless steel, a rigid polymer, or the like. Alternatively, the internal tube may comprise a non-metallic material (e.g., biocompatible polymer) that is assembled into the generally rigid needle body 146. It should be understood that, in other embodiments, the first and second lumens 142 and 144 may be arranged in the cannula 140 in a manner other than coaxial. For example, the first and second lumens 142 and 144 may be arranged in a side-by-side configuration (refer, for example, the embodiment described in connection with to FIG. 3).

Still referring to FIG. 2, the first lumen 142 is in fluid communication with the first set of side ports 145a such that the first thermochemical ablation agent 115 can be delivered through the first lumen 142 and out through the side ports 145a. Also, the second lumen 144 is in fluid communication with the second set of side ports 145b such that the second thermochemical ablation 125 agent can be delivered through the second lumen 144 and out through the side ports 145b. The walls that at least partially defines the first and second lumens (e.g., in this embodiment, the needle body 146 and the internal tube 147) are configured to maintain the reagents 115 and 125 separate from one another until they reach the distal portion 134 and are dispensed from the ports 145a-b. Upon dispensation from the side ports 145a-b, the thermochemical ablation reagents 115 and 125 can mix with one another to generate an exothermic chemical reaction—thereby using chemical reaction energy to ablate the targeted tissue.

In this embodiment, the cannula 140 includes a closed distal end 143. As such, the thermochemical ablation reagents 115 and 125 are dispensed from the side ports 145a-b rather than from end ports in the distal end 143. In some embodiments, the distal end may be formed with one or more end ports, and those end ports are plugged or otherwise sealed to ensure that the thermochemical ablation reagents 115 and 125 are dispensed only from the side ports 145a-b. As previously described, the side ports 145a-b can be used to radially disperse the first and second thermochemical ablation reagents 115 and 125, which can improve the mixing of the reagents 115 and 125 upon exiting cannula 140 (e.g., due to increased turbulence) and can more evenly distribute the heat generated by the mixing of the reagents 115 and 125.

Still referring to FIG. 2, some embodiments of the fluid delivery device 130 may include one or more sensors arranged on the distal portion 134. For example, in this embodiment, the distal portion 134 includes at least one temperature sensor 148 disposed at or near an outer surface of the cannula 140. The temperature sensor 148 may comprise a thermocouple instrument, such as a type K thermocouple, that has leads incorporated into the body of the cannula 140 (e.g., electrical lines embedded into the walls, insulated electrical traces formed on an inner or outer wall, or the like). The leads may extend from the temperature sensor 148 back to the proximal portion 132 (FIG. 1) of the fluid delivery device 130 so as to connect with a sensor computer system (not shown in FIGS. 1-2). The sensor computer system may be configured to indicate a temperature of the tissue disposed near the temperature sensor 148 based upon signals communicated from the temperature sensor 148. Such temperature information may be used, for example, by a physician or other user during the procedure to monitor the ablation of the targeted tissue.

In another example of a sensor, the distal portion 134 of the delivery device 130 may include at least one pH sensor 149 arranged disposed proximate an outer surface of the cannula 140. The temperature sensor 149 may comprise a pH probe instrument that has an electrical lead incorporated into the body of the cannula 140 (e.g., electrical lines embedded into the walls, insulated electrical traces formed on an inner or outer wall, or the like). The lead may extend from the pH sensor 149 back to the proximal portion 132 (FIG. 1) of the fluid delivery device 130 so as to connect with a sensor computer system (not shown in FIGS. 1-2). The sensor computer system may be configured to indicate a pH level of the material proximate the distal portion based upon signals communicated from the pH sensor 149. Such pH information may be used, for example, by a physician or other user during the procedure to monitor the acid load applied to the tissue during the delivery of the thermochemical ablation reagents 115 and 125.

Referring now to FIG. 3, some embodiments of the fluid delivery device may include a multi-lumen cannula in which at least one lumen is not arranged in a coaxial configuration. In this embodiment, an alternative distal portion 134' of the fluid delivery device includes a cannula 240 having at least two lumens 242 and 244 in a non-coaxial configuration. The first lumen 242 is arranged adjacent to the second lumen 244. For example, the first and second lumens 242 and 244 may be at least partially defined by two adjacent bores form through the cannula 140. In such circumstances, the cannula 140 may comprise a generally rigid needle body 246 in which the first and second lumens 242 and 244 are formed and thereby separated by an intermediate wall portion 247.

Accordingly, the walls that at least partially define the lumens (e.g., in this embodiment, the needle body 246 and the intermediate wall portion 147) are configured to maintain the reagents 115 and 125 separate from one another until they reach the distal portion 134'. Thereafter, the first and second reagents 115 and 125 can at least partially mix (via internal ports 248a and 248b) before dispensing from the cannula 240. The first internal port 248a permits a portion of the first reagent 115 from the first lumen 242 to pass into the second lumen 244 in order to mix with a portion of the second reagent 125 in the distal portion 134'. Also, the second internal port 248b permits a portion of the second reagent 125 from the second lumen 244 to pass into the first lumen 242 in order to mix with a portion of the first reagent 115 in the distal portion 134'. In some circumstances, a portion of the first and second reagents 115 and 125 can mix with one another within the distal portion 134', and other portions of the first and second reagents 115 and 125 can mix after being dispensed from the ports of the distal portion 134'. By mixing at least a portion of the first and second thermochemical ablation reagents 115 and 125 in the distal portion 134' before dispensation into the targeted tissue, some portion of the dispensed fluid can be heated from the exothermic chemical reaction immediately before dispensation into the targeted tissue. It should be understood that, in other embodiments, the cannula 240 may not include the internal ports 248a-b so that the first and second reagents 115 and 125 do not mix within the distal portion 134' (e.g., mix after being dispensed from the distal portion 134').

Similar to previously described embodiments, the distal portion 134' may include one or more side ports 245a-b in the cannula 240 that can be used to radially disperse the first and second thermochemical ablation reagents 115 and 125. This radial dispersion of the thermochemical ablation reagents 115 and 125 can be used to mix at least a portion of the reagents 115 and 125 in the region proximate the distal portion 134' and that thereby generate an exothermic chemical reaction for ablating the targeted tissue. Further, the radial dispersion of the fluid from the side ports 245a-b can be used to more evenly distribute the heat energy from the exothermic chemical reaction. As shown in FIG. 3, a first set of side ports 245a extend from the first lumen 242, a second set of side ports 245b extend from the second lumen 244. The number of first side ports 245a and second side ports 245b may be different than that depicted in FIG. 3.

Still referring to FIG. 3, in this embodiment, the cannula 240 includes a distal end having end ports 243a and 243b. The first end port 243a extends from the first lumen 242 such that the first thermochemical ablation agent 115 (and the portion of the combined first and second reagent 115 and 125 mixed via the internal port 248b) can be delivered through the first lumen 242 and out through the first end port 243a. Also, the second end port 243b extends from the second lumen 244 such that the second thermochemical ablation agent 125 (and the portion of the combined first and second reagent 115 and 125 mixed via the internal port 248a) can be delivered through the second lumen 244 and out through the second end port 243b. Thus, the thermochemical ablation reagents 115 and 125 can be dispensed from the end ports 243a and 243b in addition to side ports 245a and 245b. When the unmixed portion of the first reagent 115 is delivered through the first end port 243a and the unmixed portion of the second reagent 125 is delivered from the second end port 243b, the unmixed portions of reagents 115 and 125 can subsequently mix and react with one another in a region distal of the cannula 240. In these circumstances, the physician or other user can manipulate the cannula 240 so as to delivery the thermochemical ablation energy to regions radially outward from the distal portion 134' and distally forward of the distal portion 134'. It should be understood that, in some embodiments, the cannula 240 having non-coaxial lumens 242 and 244 may include a closed distal end similar to that described in connection with FIG. 2.

In particular embodiments, the distal portion 134' of the fluid delivery device may include one or more sensors arranged on the cannula 240. For example, the cannula 240 may incorporate a temperature sensor (e.g., sensor 148 described in connection with FIG. 2), a pH sensor (e.g., sensor 149 described in connection with FIG. 2), or the like. Such sensors may provide useful information to the physician or other user during the ablation procedure.

In alternative embodiments, the cannula 240 may include end ports 243a-243b without any side ports 245a-b. In such embodiments, one or more end ports 243a may extend from the first lumen 242, and one or more end ports 243b may extend from the second lumen 244. The first and second thermochemical ablation reagents 115 and 125 would be delivered to the end ports 243a-b without an opportunity to pass through side ports 245a-b. Such a configuration may be used, for example, to ablate a specific and localized region of targeted tissue that is disposed generally distal of the tip of the cannula 240. It should be understood that, in these embodiments, the first and second lumens may be arranged in a coaxial configuration, in a side-by-side configuration, or a different configuration.

Figure 4:
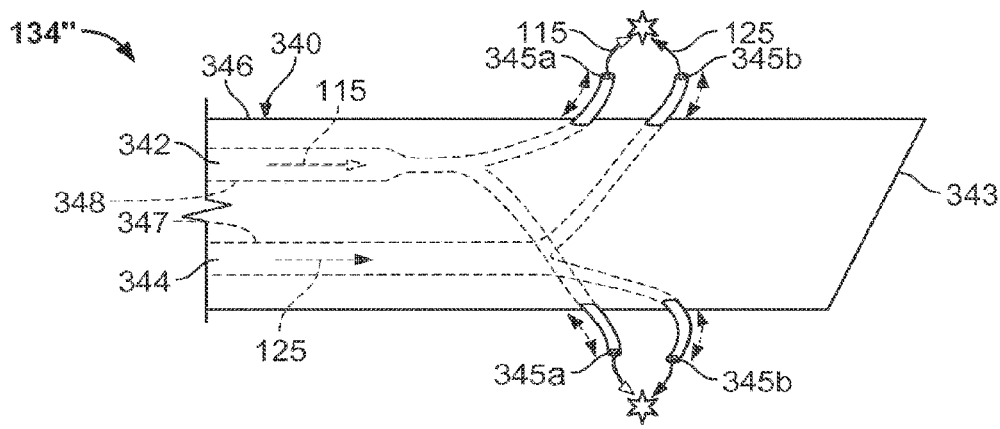
FIG. 4 is a cross-sectional view of a portion of yet another alternative delivery cannula for a thermochemical ablation system, in accordance with some embodiments.

Referring now to FIG. 4, some embodiments of the fluid delivery device may include a cannula with adjustable side projections that dispense the thermochemical ablation reagents 115 and 125. In this embodiment, an alternative distal portion 134" of the fluid delivery device includes a cannula 340 having at least two lumens 342 and 344 that can be adjusted relative to an outer needle body 346. For example, the first lumen 342 may be at least partially defined by a first tube 348 that can be actuated from a proximal position to a distal position so that first side projections 345a protrude outwardly from the radial surface of the cannula 340. Similarly, the second lumen 344 may be at least partially defined by a second tube 347 that can be actuated from a proximal position to a distal position so that second side projections 345*b* protrude outwardly from the radial surface of the cannula 340. The first and second side projections 345*a-b* may include ports therein that dispense the first and second thermochemical ablation reagents 115 and 125 from the projections. Accordingly, the first and second side projections 345*a-b* can be adjusted from a retracted position (e.g., a position generally within a bore of the outer needle body 346) to an extended position (e.g., refer to FIG. 4) so as to penetrate into a wider region of the targeted tissue and further distribute the thermochemical ablation energy during delivery of the reagents 115 and 125.

In this embodiment, the outer needle body 346 comprises a generally rigid material (e.g., stainless steel or the like) and the first and second tubes 348 and 347 comprise a shape memory alloy that exhibits superelastic characteristics when inside the patient's body. For example, the first and second tubes 348 and 347 may comprise nitinol material or the like, which provides superelastic flexibility during the transition from the retracted position (e.g., the side projections 345*a-b* are constrained generally within a bore of the outer needle body 346) to the extended position (e.g., refer to FIG. 4). As such, the side projections 345*a-b* may have a curved shape or other configured that permits the ports of the side projections to be pointed toward particular regions.

In use, a physician or other user can direct the distal portion 134" to the targeted tissue under guidance from a medical imaging system 190 (FIG. 1). In such circumstances, the side projections 345*a-b* may be in the retracted position to facilitate insertion of the cannula 340 into the patient. When the targeted tissue is reached by the distal portion 134", the physician or other user may operate a trigger device or other actuator (not shown in FIG. 4) that causes the first and second tubes 348 and 347 to shift positions relative to the outer needle body 346. For example, the trigger device may cause the first and second tubes 348 and 347 to adjust distally, thereby forcing the side projections 345*a-b* to the extended position radially outward of the cannula 340. As such, the side projections 345*a-b* act as tines that penetrate into a wider region of the targeted tissue. Thereafter, the physician or other user can adjust the coupler 119 (FIG. 1) or other device so that the first and second thermochemical ablation reagents 115 and 125 are dispensed out of the ports in the side projections 345*a-b*. Upon release from the ports, the first and second thermochemical ablation reagents 115 and 125 are mixed with one another in a chemical reaction that generates heat to ablate the targeted tissue.

It should be understood that, in some embodiments, the cannula 340 may have lumens 342 and 344 that are arranged in a coaxial configuration, in a side-by-side configuration, or in a different configuration. In alternative embodiments, the first and second thermochemical ablation reagents 115 and 125 may be at least partially mixed in the distal portion 134" immediately before being dispensed from the ports of the side projections 345*a-b* (e.g., similar to embodiments described in connection with FIG. 3). Also, in some embodiments, the cannula 340 may have a number of side ports to dispense the first and second reagents directly from the cannula 340 (in addition to the fluid delivery from the side projections 345*a-b*). Further, in some embodiments, the cannula 340 may have a closed distal end similar to that described in connection with FIG. 2 or end ports similar to those described in connection with FIG. 3. In particular embodiments, the distal portion 134" of the fluid delivery device may include one or more sensors arranged on the cannula 340. For example, the cannula 340 may incorporate a temperature sensor (e.g., sensor 148 described in connection with FIG. 2), a pH sensor (e.g., sensor 149 described in connection with FIG. 2), or the like. Such sensors may provide useful information to the physician or other user during the ablation procedure.

Referring now to FIG. 5, some embodiments of a thermochemical ablation system 400 may include a fluid delivery device 430 having a cannula 440 that is at least partially flexible. For example, the cannula 440 may comprise a flexible catheter body 446 that is deliverable through a bodily passageway 45, including a vein, an artery, a urethra, a rectum, a vagina, an esophagus, or the like. Accordingly, a physician or other user can direct a distal portion 434 of the fluid delivery device 430 through the bodily passageway 45 and toward a targeted tissue 50' (e.g., a tumor, a vasculature occlusion such as varicoceles or varicose veins, a ureteral occlusion, or the like) for ablation or other treatment of the targeted tissue 50'.

Similar to previously described embodiments, the thermochemical ablation system 400 includes a first fluid reservoir 410 and a second fluid reservoir 420 that are in fluid communication with the thermochemical ablation device 430. The first reservoir 410 includes the first thermochemical ablation reagent 115, and the second reservoir 420 includes the second thermochemical ablation reagent 125. Each of the reservoirs 410 and 420 includes an actuator 412 and 422 that can be adjusted to provide a dispensing force to the reagents 115 and 125. The first actuator 412 and the second actuator 422 can be mechanically coupled to one another with a coupling 419 so that both actuators 412 and 422 can be simultaneously adjusted.

Similar to previously described embodiments, the cannula 340 of the fluid delivery device 430 includes a first lumen 442 in fluid communication with the first reservoir 410 and a second lumen 444 in fluid communication with the second reservoir 420. Also, the distal portion 434 of the delivery device 430 may include a plurality of fluid ports 445*a-b* to disperse the first and second thermochemical ablation reagents 115 and 125 and thereby mix the reagents 115 and 125 in the region proximate the distal portion 434.

Still referring to FIG. 5, this embodiment of the fluid delivery device 430 includes the cannula 440 in the form of a flexible catheter device. For example, the cannula 440 may includes a generally flexible catheter body 446 comprised of a biocompatible polymer. The fluid delivery device 430 may include a steering mechanism (e.g., steering wires, shape memory actuators, or the like) so that the distal tip of the cannula 440 can be navigated through the bodily passageway 45. The cannula 440 may also include an internal tube 447 that is formed inside the catheter body 446. As such, the first lumen 442 is at least partially defined by the internal tube 447, and the second lumen 444 is at least partially defined between the catheter body 446 and the internal tube 447. Thus, in this embodiment, the first and second lumens 442 and 444 are arranged in a coaxial configuration. In other embodiments, the first and second lumens 442 and 444 can be arranged in a side-by-side configuration or in other configurations.

The distal portion 434 of the fluid delivery device 430 may include one or more side ports 445*a-b* through which the first and second reagents 115 and 125 are dispensed into the targeted tissue 50'. The side ports 445*a-b* may be oriented so that the thermochemical ablation reagents 115 and 125 are radially dispersed from the distal portion 432. Such radial dispersion of the thermochemical ablation reagents may provide improved mixing of the reagents 115 and 125 upon exiting the fluid delivery device 430 (e.g., due to increased turbulence). Furthermore, the radial dispersion through the side ports 445*a-b* can more evenly distribute the heat generated by the mixing of the reagents 115 and 125. It should be understood that, in some embodiments, the cannula 440 may have a closed distal end similar to that described in connection with FIG. 2 or end ports similar to those described in connection with FIG. 3. Also, in alternative embodiments, the cannula 440 may include end ports without any side ports 445*a-b*. In particular embodiments, the distal portion 434 of the fluid delivery device 430 may include one or more sensors arranged on the cannula 440. For example, the cannula 440 may incorporate a temperature sensor (e.g., sensor 148 described in connection with FIG. 2), a pH sensor (e.g., sensor 149 described in connection with FIG. 2), or the like. Such sensors may provide useful information to the physician or other user during the ablation procedure.

As shown in FIG. 5, the first set of side ports 445*a* may be in fluid communication with the first lumen 442 so that the first thermochemical ablation reagent 115 is evacuated from the side ports 445*a* when the coupler 419 (and first actuator 412) is adjusted. Likewise, the second set of side ports 445*b* may be in fluid communication with the second lumen 444 so that the second thermochemical ablation reagent 125 is evacuated from the side ports 445*b* when the coupler 419 (and second actuator 412) is adjusted. Accordingly, the fluid delivery device 430 provides for simultaneous infusion of the first and second reagents 115 and 125 into the targeted tissue 50', during which the thermochemical ablation reagents 115 and 125 mix with one another to cause an exothermic chemical reaction. The heat generated from this chemical reaction may be sufficient to ablate at least a portion of the targeted tissue 50' surrounding the distal portion 434 of the fluid delivery device 430. As previously described, the byproducts of the chemical reaction may include greater heat generation with lower acid (or base) load toxicity because the fluid delivery device 430 infuses two reagents that chemically react with one another (rather than direct injection of a single acidic reagent). It should be understood that, in some embodiments, the first and second thermochemical ablation reagents 115 and 125 may be at least partially mixed (via internal ports) in the distal portion 434 immediately before being dispensed from the side ports 445*a-b* (as described, for example, in connection with FIG. 3).

Still referring to FIG. 5, the fluid delivery device 430 may optionally include an expandable balloon device 441 disposed along the distal portion 434. The expandable balloon device 441 may be used to anchor the distal tip of the cannula 340 in a desired location with the bodily passage way 45. Alternatively, the expandable balloon may be used to temporarily seal the bodily passageway 45 during the delivery of the thermochemical ablation reagents 115 and 125 from the catheter body 446. For example, the balloon 441 may be filled in saline or another fluid to press against the wall of a vein or artery, thereby temporarily hindering blood flow through that portion of the vein or artery. The thermochemical ablation reagents 115 and 125 can be dispensed as previously described while the balloon 441 is expanded, which permits the reagents 115 125 to mix with one another in proximity to the targeted tissue and without being carried away by ordinary blood flow. After the ablation procedure is completed, the balloon may be collapse for removably of the fluid delivery device 430.

Some embodiments of the thermochemical ablation system 400 may include a medical imaging system that provides real-time monitoring of the device 430 insertion and the delivery of the reagents 115 and 125. For example, the medical imaging system can include an ultrasound imaging system 190 (refer, for example, to FIG. 1) to enable a physician or other user to view the distal portion 434 of the fluid delivery device 430 in the targeted tissue 50'. In another example, the medical imaging system may include a CT imaging system or the like. The delivery device 430 may comprise one or more materials that are compatible with the selected imaging system so as to enable monitoring of the delivery device 430 during insertion. For example, the cannula 440 may comprise a metallic material that can be visualized using the ultrasound imaging system 190. In another example, the catheter body 446 of the cannula 440 may include magnetic resonance markers inserted therein which provide viewability using the selected imaging system. Furthermore, in some embodiments, the delivery device 430 may include depth markers that are directly viewable to the physician or other user. For example, the outer catheter body 446 may include a number of depth markers. The physician or other user can view these depth markers during insertion of the cannula 140 through the skin 40 to indicate the approximate depth of insertion. Accordingly, a physician or other user can direct a distal portion 434 of the fluid delivery device 430 through the bodily passage-way 45 and toward a targeted tissue 50' (e.g., a tumor, a vasculature occlusion such as varicoceles or varicose veins, a ureteral occlusion, or the like) for ablation or other treatment of the targeted tissue 50'.

The thermochemical ablation systems described herein may be employed in minimally invasive techniques to ablate solid tumors or other targeted tissue. These ablation techniques may induce chemical reactions to generate heat for ablation energy. Such chemical reactions may be induced by mixing at least one acid reagent and at least one base reagent, which can neutralize or otherwise reduce the acid load applied to the patient during the procedure. As previously described, other reagents can be used to induce the desired exothermic chemical reaction. The thermochemical ablation techniques described herein can be used to treat solid tumors that arise in number of circumstances, including liver cancer, lung cancer, renal cancer, breast cancer, prostate cancer, sarcomas, or the like. Furthermore, the thermochemical ablation techniques described herein can be used to treat other targeted tissue, such as occlusions that arise in bodily passage ways. Finally, the thermochemical ablation techniques described herein are not limited to use in human patients. For example, the thermochemical ablation systems described herein may be used to treat other animal patients, including mammalian patients.

A number of embodiments of the invention have been described. Nevertheless, it will be understood that various modifications may be made without departing from the spirit and scope of the invention. Accordingly, other embodiments are within the scope of the following claims.

What is claimed is:

1. A thermochemical ablation system, comprising:
a percutaneous fluid delivery cannula comprising first and second lumens extending from a proximal portion to a distal portion, the distal portion comprising a first exterior port along a distal exterior portion of the percutaneous fluid delivery cannula and a second exterior port along the distal exterior portion of the percutaneous fluid delivery cannula, the first exterior port being in fluid communication with the first lumen, and the second exterior port in fluid communication with the second lumen;

first means for containing a first thermochemical ablation liquid and communicating the first thermochemical ablation liquid through the first lumen to the first exterior port along the distal exterior portion of the percutaneous fluid delivery cannula; and second means for containing a second thermochemical ablation liquid and communicating the second thermochemical ablation liquid through the second lumen to the second exterior port along the distal exterior portion of the percutaneous fluid delivery cannula so that the second thermochemical ablation liquid is isolated from the first thermochemical ablation liquid before exiting from the second exterior port of the percutaneous fluid delivery cannula, the second thermochemical ablation liquid being reactive with the first thermochemical ablation liquid, means for simultaneously delivering the first and second thermochemical ablation liquids out of the respective first and second exterior ports along the distal exterior portion of the percutaneous fluid delivery cannula to provide simultaneous dispersion and mixing of the first and second thermochemical ablation liquids proximate to the distal exterior portion, the second thermochemical ablation liquid being reactive with the first thermochemical ablation liquid to generate tissue ablation heat via an exothermic chemical reaction.

2. The system of claim 1, wherein the means for simultaneous delivery comprises: a first actuator to deliver liquid from the first means for containing, and a second actuator to deliver liquid from the second means for containing, the first and second actuators being coupled to one another so as to provide simultaneous actuation.

3. The system of claim 1, wherein the first thermochemical ablation liquid comprises an acid contained in the first means for containing.

4. The system of claim 3, wherein the first thermochemical ablation liquid comprises an acid selected from the group consisting of acetic acid, peracetic acid, hydrochloric acid, hydrobromic acid, hydriodic acid, sulfuric acid, nitric acid, nitrous acid, perchloric acid, phosphoric acid, oxalic acid, pyruvic acid, malonic acid, and amino acids.

5. The system of claim 3, wherein the second thermochemical ablation liquid comprises a base contained in the first means for containing.

6. The system of claim 5, wherein the second thermochemical ablation liquid comprises base selected from the group consisting of KOH, NaOH, $NH_4OH$, $Ca(OH)_2$, $NaHCO_3$, $K_2CO_2$, BuLi, NaOEt or NaSEt, NaH, KH, and amines.

7. The system of claim 1, wherein the first thermochemical ablation liquid comprises an electrophile selected from the group consisting of acetic anhydride, acetyl chloride, and acetyl bromide, and the second thermochemical ablation liquid comprises a nucleophile.

8. The system of claim 1, wherein the percutaneous fluid delivery cannula comprises a generally rigid injection needle.

9. The system of claim 8, wherein the injection needle comprises an outside diameter of about 0.134 inches or less.

10. The system of claim 1, wherein the percutaneous fluid delivery cannula comprises a flexible catheter.

* * * * *